US00PP15950P3

(12) United States Plant Patent
Bourne

(10) Patent No.: US PP15,950 P3
(45) Date of Patent: Sep. 13, 2005

(54) EUROPEAN PLUM NAMED '92-95-99'

(50) Latin Name: *Prunus domestica*
Varietal Denomination: 92-95-99

(75) Inventor: Timothy F. Bourne, Visalia, CA (US)

(73) Assignee: Sunview Vineyards of California, Inc., Delano, CA (US)

( * ) Notice: Subject to any disclaimer, the term of this patent is extended or adjusted under 35 U.S.C. 154(b) by 159 days.

(21) Appl. No.: 10/280,572

(22) Filed: Oct. 24, 2002

(65) Prior Publication Data

US 2004/0083509 P1 Apr. 29, 2004

(51) Int. Cl.[7] ..... A01H 5/00

(52) U.S. Cl. ..... Plt./184

(58) Field of Search ..... Plt./184

*Primary Examiner*—Kent Bell
*Assistant Examiner*—Louanne Krawczewicz Myers
(74) *Attorney, Agent, or Firm*—Jondle & Associates P.C.

(57) ABSTRACT

A new and distinct variety of European plum (*Prunus domestica*) cv. '92-95-99' is described herein. The new variety ripens in late mid-season in the Delano, Calif. area with large, bright red fruit and firm flesh. Ripened fruit attains a very high level of sugar and holds in cold storage very well.

3 Drawing Sheets

Genus and Species *Prunus domestica*.
Variety denomination: '92-95-99'.

BACKGROUND AND SUMMARY OF THE INVENTION

The invention described here is a new variety of plum, *Prunus domestica* cv. '92-95-99'. The seedling originates from a planned cross in 1993 in Tulare County, Calif. The new variety is characterized by having large, bright red elliptic fruits which ripen in mid-August in the Delano, Calif. area. The high quality fruit has firm texture, good storage characteristics, and is very sweet, making it suitable for the fresh market.

The emasculated seed parent was the variety 'Sugar' (unpatented) and the pollen parent was the variety 'President' (unpatented). Seed from the planned cross was harvested in the summer of 1993, stratified, then planted in the spring of 1994 in Kern County near the city of McFarland, Calif. The original tree was selected in 1996 and was then budded to nematode-resistant 'Myrobalan 29C' rootstock (unpatented) in a two tree plot (2 m×3 m spacing) near McFarland, Calif. In 1998, a forty tree plot was cleft grafted from wood of the two tree plot and the original tree using 'Myrobalan 29C' rootstock (unpatented) (3.7 m×3.7 m spacing) near Delano, Calif. Observations of trees from these propagations indicate that the characteristics are firmly fixed and all trees reproduced true to type in successive generations of asexual reproduction.

COMPARISON WITH PARENTAL CULTIVAR

The new variety is intermediate in its characteristics between its two parents. It ripens about one week later than 'Sugar' (unpatented) and two weeks before 'President' (unpatented) in the Delano area. The very vigorous trees of this new variety are well adapted to the hot climate of the southern Central Valley of California.

DESCRIPTION OF THE FIGURES

The accompanying photographs illustrate the following.

DETAILED BOTANICAL DESCRIPTION OF THE INVENTION

Figure 1:
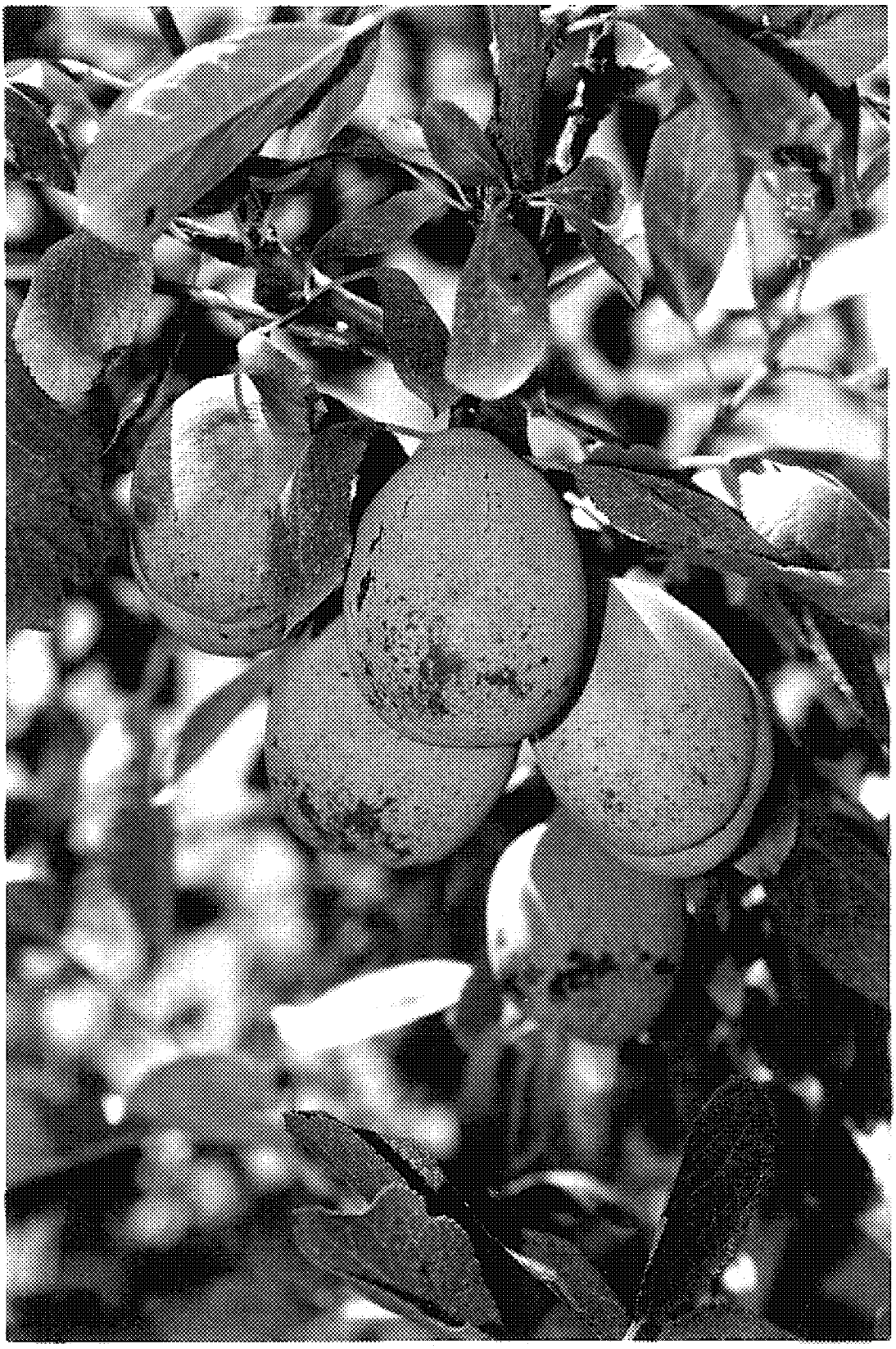
FIG. 1 shows a close-up view of fruit and leaves of the variety.
Figure 2:
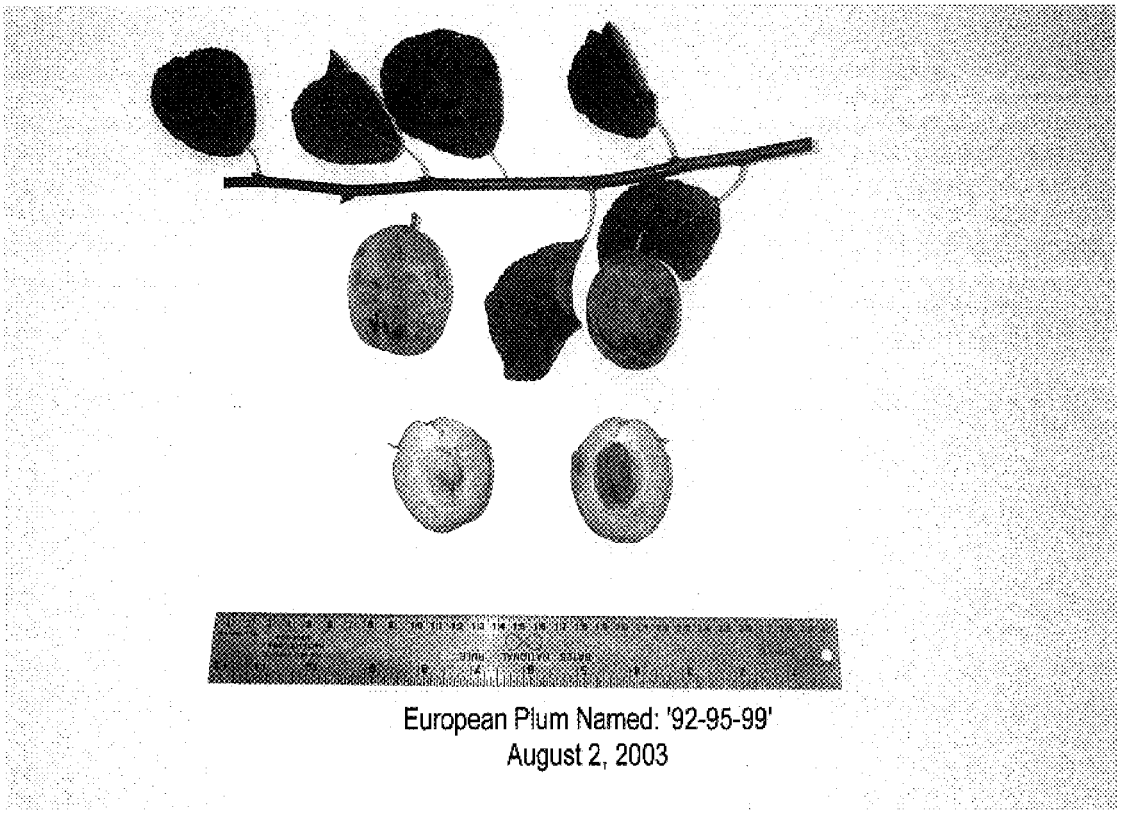
FIG. 2 shows the harvested fruit and branch from the tree.
Figure 3:
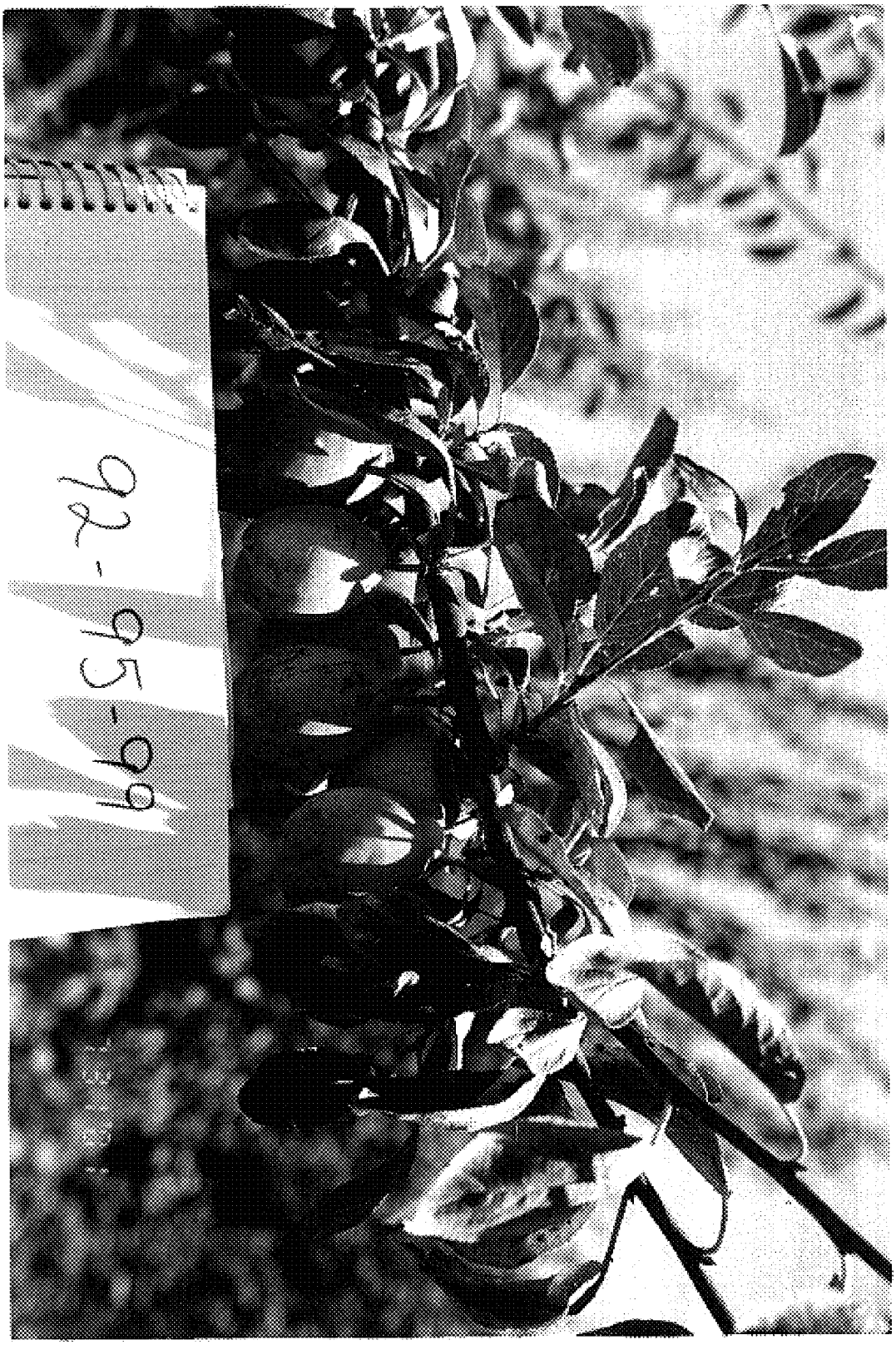
FIG. 3 shows fruit and leaves of the variety on a branch.

The following description of European plum '92-95-99' contains references to color names taken from the Munsell Color Chart for Plant Tissues, published by Munsell Color, New Windsor, N.Y. Descriptors conform to the International Board for Plant Genetic Resources, Commission of European Communities: Committee on Disease Resistance Breeding and Use of Genebanks, 1984. The characteristics listed below were obtained from the 10 year old original tree and the 6 year old grafted trees grown in the McFarland and Delano, Calif. area.

Tree:

*Habit.*—Upright.

*Tree height.*—3.5 m at 2 years of age.

*Productivity.*—Very productive, appears to require a pollinizer. 6-year-old trees averaged 27.3 kg of fruit per tree.

*Rootstock.*—Myrobalan 29C, nematode resistant (unpatented).

Trunk:

*Original tree trunk diameter.*—Tree at 10 years in 0.6 m×3 m row spacing=9.1 cm when measured at 1.2 m from the soil surface.

*Grafted tree trunk diameter.*—Tree at 6 years in 2 m×3 m row spacing on 'Myrobalan 29C' rootstock (unpatented)=6.1 cm when measured at 45 cm from the soil surface.

*Bark texture.*—Very rough.

*Trunk color.*—5YR 4/6 to 4/8 (brown).

*Trunk lenticel color.*—5YR 6/10 (orange).
*Trunk lenticel length.*—5–7 mm.
*Trunk lenticel number.*—Variable: many sectors with none up to 2 per square centimeter.

Branches:
*Branch diameter.*—Diameter at 50 cm from crotch=3.6 cm. (6-year-old trees at 2 m×3 m row spacing on 'Myrobalan 29C' rootstock).
*Color of 1 year old wood.*—5YR 4/4 to 4/6.
*Color of 3 year old wood.*—10R 5/2.
*Texture of 3 year old wood.*—Rough, though less so than trunk.
*Lenticels.*—About 1 mm in diameter; approximately 12 per square cm.
*Lateral branching on first year branches.*—Uncommon.
*Branch length.*—New shoot lengths range from 51–160 cm at end of growing season on grafted trees.
*Internode length.*—2.7–3.7 cm on most portions of the stems except toward the tips of the stems where internode length is much shorter.

Buds:
*Observed bud hardiness.*—No bud damage observed at 0 C.
*Vegetative bud shape.*—Conical.
*Vegetative bud length.*—6 mm.
*Vegetative bud diameter.*—3 mm.
*Vegetative bud color.*—10R 3/4.
*Vegetative bud surface.*—Sparsely pubescent.
*Flower bud shape.*—Conical.
*Flower bud length.*—3 mm.
*Flower bud diameter.*—1.5 mm.
*Flower bud color.*—10R 3/6.
*Flower bud surface.*—Glabrous, glossy.
*Flower bud number.*—Usually two per node.

Leaves:
*Leaf arrangement.*—Alternate, one leaf per node. Most leaves arise 120 degrees from the previous leaf, repeating approximate stem position with every fourth leaf.
*Blade length.*—9.5 cm.
*Blade width.*—5.9 cm.
*Petiole length.*—3.0 cm.
*Petiole diameter.*—2 mm.
*Petiole color.*—2.5 GY 8/8.
*Leaf shape.*—Elliptic, margins cupped upward.
*Leaf margins.*—Crenate.
*Teeth.*—Rounded, one side convex, one concave; about 1 mm in length.
*Leaf apex.*—Rounded to broadly acute.
*Leaf base.*—Oblique.
*Upper surface color.*—7.5GY 4/4 to 4/6 (dark green).
*Lower surface color.*—7.5GY 5/6 to 5/8 (dark green).
*Upper leaf surface texture.*—Very smooth, waxy.
*Lower leaf surface texture.*—Rough with veins being very prominent, raised.
*Erect hairs on veins of lower surface.*—Numerous.
*Erect hairs on upper surface.*—Absent.
*Erect hairs on upper surface of petiole.*—Sparse.
*Stipules.*—None.
*Glands.*—None.

Flowers:
*Date of flowering in McFarland, Calif.* (*first flowers dehisce*).—Mar. 17, 2004.
*Date of full bloom.*—Mar. 22, 2004.
*Date of last bloom.*—Mar. 28, 2004.
*Number of flowers per bud.*—1–3.
*Flower diameter.*—18 mm.
*Petal color* (*both upper and lower surfaces*).—2.5GY 10/0.
*Petal number.*—5.
*Petal length.*—10 mm.
*Sepal color.*—5GY 7/8.
*Sepal number.*—5.
*Sepal length.*—7 mm.
*Flower type.*—Perfect.
*Anther color.*—5Y 8/12 (yellow).
*Pollen color.*—5Y 8/10 (yellow).
*Carpels.*—1–2 per flower.
*Fertility.*—Appears to be partially self-incompatible.
*Fragrance.*—Typical of European plums, faintly aromatic.

Fruit:
*Harvest maturity.*—Mid-season. First harvest: Jul. 22, 2004. Last harvest: Jul. 29, 2004.
*Skin color.*—2.5R 4/10 (bright red) with sectors 2.5Y 8/12 (yellow).
*Flesh color.*—7.5YR 7/12 (yellow-orange).
*Length.*—4.5 cm.
*Width.*—4.0 cm.
*Weight.*—52.2 g.
*Refractometer test.*—21.9 brix.
*Pressure at harvest* (*penetrometer test*).—13.3 lbs.
*Configuration.*—Oval.
*Apex.*—Rounded.
*Pistil point.*—Smooth.
*Skin thickness.*—Thin, typical of European plum.
*Skin texture.*—Smooth.
*Tendency to crack.*—None.
*Juiciness of flesh.*—Very juicy.
*Flavor.*—Mild and sweet, typical of European plum.
*Aroma.*—Mild.
*Fruit flesh texture.*—Crisp.
*Fibers in flesh.*—None.
*Ripening.*—Uniform throughout the fruit.
*Eating quality.*—Good.
*Use.*—Fresh market.
*Keeping quality.*—Good, fruit has held well in storage for four weeks.
*Shipping quality.*—Good.

Stone:
*Stone adherence to flesh.*—Clingstone.
*Stone shape.*—Elliptic with wings on either side of long edge.
*Fibers.*—None.
*Surface.*—Rough.
*Color.*—5YR 5/8 to 5/10 (orangish brown).
*Length.*—2.5 cm.
*Width.*—1.6 cm.
*Thickness.*—0.7 cm.

Kernel:
*Kernel color.*—5YR 5/6.
*Kernel length.*—18 mm.
*Kernel width.*—10 mm.
*Viability.*—Unknown.
*Astringency.*—None.
*Amygdaline.*—Has pleasant, pronounced almond flavor.

Disease resistance: Typical of European plums; no problems seen in the original tree or grafted plants in 10 years of observations.

What is claimed is:

1. A new and distinct variety of European plum plant named '92-95-99' herein described and illustrated.

* * * * *